(12) United States Patent
Schneider-Fresenius et al.

(10) Patent No.: US 6,572,853 B1
(45) Date of Patent: Jun. 3, 2003

(54) RECOMBINANT HUMAN BETA INTERFERON WITH ENHANCED SOLUBILITY

(75) Inventors: Christian Schneider-Fresenius, Hannover (DE); Bernd Otto, Hannover (DE); Gero Waschutza, Meinersen (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 09/403,532
(22) PCT Filed: Apr. 16, 1998
(86) PCT No.: PCT/EP98/02238
§ 371 (c)(1), (2), (4) Date: Feb. 22, 2000
(87) PCT Pub. No.: WO98/48018
PCT Pub. Date: Oct. 29, 1998

(30) Foreign Application Priority Data

Apr. 23, 1997 (DE) .......................... 197 17 864

(51) Int. Cl.[7] .................. A61K 38/21; C07K 14/00; C12P 21/04
(52) U.S. Cl. .................... 424/85.6; 424/85.4; 530/351; 435/69.51; 435/71.1
(58) Field of Search .................. 530/351; 424/85.4, 424/85.6; 435/69.51, 71.1

(56) References Cited

U.S. PATENT DOCUMENTS

| | | | |
|---|---|---|---|
| 4,588,585 A | | 5/1986 | Mark et al. |
| 5,350,836 A | * | 9/1994 | Kopchick et al. ........... 530/399 |

FOREIGN PATENT DOCUMENTS

| | | |
|---|---|---|
| EP | 0 163 993 | 5/1985 |

OTHER PUBLICATIONS

Kruse et al., EMBO J., 1993, vol. 12, No. 13, pp. 5121–5129.*

* cited by examiner

*Primary Examiner*—Yvonne Eyler
*Assistant Examiner*—Janet L. Andres
(74) *Attorney, Agent, or Firm*—Barnes & Thornburg

(57) ABSTRACT

The invention relates to variants of recombinant human beta interferon and to a method for the production thereof, wherein at least one of the following amino acids Leu(5), Phe(8), Phe(15), Leu(47), Phe(50), Leu(106), Phe(111), Leu(116), Leu(120) and Phe(156) is exchanged with hydrophilic amino acid with a hydroxy group, specially serine, tyrosine or threonine, resulting in enhanced hydrophilic property of the protein surface.

9 Claims, 4 Drawing Sheets

| | | | | | | | | | | | |
|---|---|---|---|---|---|---|---|---|---|---|---|
| Met 1 | Ser | Tyr | Asn | Leu 5 | Leu | Gly | Phe | Leu | Gln 10 | Arg | Ser |
| Ser | Asn | Phe 15 | Gln | Cys | Gln | Lys | Leu 20 | Leu | Trp | Gln | Leu | Asn 25 |
| Gly | Arg | Leu | Glu | Tyr 30 | Cys | Leu | Lys | Asp | Arg 35 | Met | Asn | Phe |
| Asp | Ile 40 | Pro | Glu | Glu | Ile | Lys 45 | Gln | Leu | Gln | Gln | Phe 50 | Gln |
| Lys | Glu | Asp | Ala 55 | Ala | Leu | Thr | Ile | Tyr 60 | Glu | Met | Leu | Gln |
| Asn 65 | Ile | Phe | Ala | Ile | Phe 70 | Arg | Gln | Asp | Ser | Ser 75 | Ser | Thr |
| Gly | Trp | Asn 80 | Glu | Thr | Ile | Val | Glu 85 | Asn | Leu | Leu | Ala | Asn 90 |
| Val | Tyr | His | Gln | Ile 95 | Asn | His | Leu | Lys | Thr 100 | Val | Leu | Glu |
| Glu | Lys 105 | Leu | Glu | Lys | Glu | Asp 110 | Phe | Thr | Arg | Gly | Lys 115 | Leu |
| Met | Ser | Ser | Leu 120 | His | Leu | Lys | Arg | Tyr 125 | Tyr | Gly | Arg | Ile |
| Leu 130 | His | Tyr | Leu | Lys | Ala 135 | Lys | Glu | Tyr | Ser | His 140 | Cys | Ala |
| Trp | Thr | Ile 145 | Val | Arg | Val | Glu | Ile 150 | Leu | Arg | Asn | Phe | Tyr 155 |
| Phe | Ile | Asn | Arg | Leu 160 | Thr | Gly | Tyr | Leu | Arg 165 | Asn | | |

(SEQ ID No. 1)

Fig. 1

| | | | | | | | | | | | |
|---|---|---|---|---|---|---|---|---|---|---|---|
| Met 1 | Ser | Tyr | Asn | Xaa 5 | Leu | Gly | Xaa | Leu | Gln 10 | Arg | Ser |
| Ser | Asn | Xaa 15 | Gln | Cys | Gln | Lys | Leu 20 | Leu | Trp | Gln | Leu | Asn 25 |
| Gly | Arg | Leu | Glu | Tyr 30 | Cys | Leu | Lys | Asp | Arg 35 | Met | Asn | Phe |
| Asp | Ile 40 | Pro | Glu | Glu | Ile | Lys 45 | Gln | Xaa | Gln | Gln | Xaa 50 | Gln |
| Lys | Glu | Asp | Ala 55 | Ala | Leu | Thr | Ile | Tyr 60 | Glu | Met | Leu | Gln |
| Asn 65 | Ile | Phe | Ala | Ile | Phe 70 | Arg | Gln | Asp | Ser | Ser 75 | Ser | Thr |
| Gly | Trp | Asn 80 | Glu | Thr | Ile | Val | Glu 85 | Asn | Leu | Leu | Ala | Asn 90 |
| Val | Tyr | His | Gln | Ile 95 | Asn | His | Leu | Lys | Thr 100 | Val | Leu | Glu |
| Glu | Lys 105 | Xaa | Glu | Lys | Glu | Asp 110 | Xaa | Thr | Arg | Gly | Lys 115 | Xaa |
| Met | Ser | Ser | Xaa 120 | His | Leu | Lys | Arg | Tyr 125 | Tyr | Gly | Arg | Ile |
| Leu 130 | His | Tyr | Leu | Lys | Ala 135 | Lys | Glu | Tyr | Ser | His 140 | Cys | Ala |
| Trp | Thr | Ile 145 | Val | Arg | Val | Glu | Ile 150 | Xaa | Arg | Asn | Phe | Tyr 155 |
| Phe | Ile | Asn | Arg | Leu 160 | Thr | Gly | Tyr | Leu | Arg 165 | Asn | | |

(SEQ ID No. 2)

Fig. 2

| | | | | | | | | | | | |
|---|---|---|---|---|---|---|---|---|---|---|---|
| Met 1 | Ser | Tyr | Asn | Ser 5 | Leu | Gly | Ser | Leu | Gln 10 | Arg | Ser |
| Ser | Asn | Ser 15 | Gln | Cys | Gln | Lys | Leu 20 | Leu | Trp | Gln | Leu | Asn 25 |
| Gly | Arg | Leu | Glu | Tyr 30 | Cys | Leu | Lys | Asp | Arg 35 | Met | Asn | Phe |
| Asp | Ile 40 | Pro | Glu | Glu | Ile | Lys 45 | Gln | Ser | Gln | Gln | Ser 50 | Gln |
| Lys | Glu | Asp | Ala 55 | Ala | Leu | Thr | Ile | Tyr 60 | Glu | Met | Leu | Gln |
| Asn 65 | Ile | Phe | Ala | Ile | Phe 70 | Arg | Gln | Asp | Ser | Ser 75 | Ser | Thr |
| Gly | Trp | Asn 80 | Glu | Thr | Ile | Val | Glu 85 | Asn | Leu | Leu | Ala | Asn 90 |
| Val | Tyr | His | Gln | Ile 95 | Asn | His | Leu | Lys | Thr 100 | Val | Leu | Glu |
| Glu | Lys 105 | Ser | Glu | Lys | Glu | Asp 110 | Ser | Thr | Arg | Gly | Lys 115 | Ser |
| Met | Ser | Ser | Ser 120 | His | Leu | Lys | Arg | Tyr 125 | Tyr | Gly | Arg | Ile |
| Leu 130 | His | Tyr | Leu | Lys | Ala 135 | Lys | Glu | Tyr | Ser | His 140 | Cys | Ala |
| Trp | Thr | Ile 145 | Val | Arg | Val | Glu | Ile 150 | Leu | Arg | Asn | Phe | Tyr 155 |
| Ser | Ile | Asn | Arg | Leu 160 | Thr | Gly | Tyr | Leu | Arg 165 | Asn | | |

(SEQ ID No. 3)

Fig. 3

| | | |
|---|---|---|
| L5 | 5'-CT<u>CC</u>CTTGGATTCCTACAAAGAAGC-3' | 25 (SEQ ID No. 4) |
| F8 | 5'-CTTGCTTGGAT<u>C</u>CCTACAAAGAAGC-3' | 25 (SEQ ID No. 5) |
| F15/C17 | 5'-AGCAGCAATT<u>C</u>TCAGT<u>CC</u>CAGAAGCTCC-3' | 28 (SEQ ID No. 6) |
| C17 | 5'-AGCAGCAATTTTCAGT<u>CC</u>CAGAAGCTCC-3' | 28 (SEQ ID No. 7) |
| L47 | 5'-TTAAGCAGT<u>CCC</u>AGCAGTTCCAGAAGG-3' | 27 (SEQ ID No. 8) |
| F50 | 5'-TTAAGCAGCTGCAGCAGT<u>C</u>CCAGAAGG-3' | 27 (SEQ ID No. 9) |
| L106 | 5'-GAAGAAAAA<u>TC</u>CGAGAAGAAGATTTCACC-3' | 30 (SEQ ID No.10) |
| F111 | 5'-GAAGAAAAACTGGAGAAGAAGATT<u>C</u>CACC-3' | 30 (SEQ ID No.11) |
| L116 | 5'-AAAA<u>T</u>CCATGAGCAGTCTGCACCTG-3' | 25 (SEQ ID No.12) |
| L120 | 5'-AAAACTCATGAGCAGT<u>TCC</u>CACCTG-3' | 25 (SEQ ID No.13) |
| F156 | 5'-ACTTTTACT<u>CC</u>ATTAACAGACCTACAGG-3' | 28 (SEQ ID No.14) |
| L5/F3Rev | 5'-TTGTAGCTCATATGTAAGTATTTCC-3' | 25 (SEQ ID No.15) |
| F15/C17Rev | 5'-TCTTTGTAGGAATCCAAGCAAGTTGTAGC-3' | 29 (SEQ ID No.16) |
| L47/F50Rev | 5'-TCTCCTCAGGGATGTCAAAGTTCATCC-3' | 27 (SEQ ID No.17) |
| L106/F111Rev | 5'-CAGGACTGTCTTCAGATGGTTTATCTG-3' | 27 (SEQ ID No.18) |
| L116/L120Rev | 5'-CCCCTGGTGAAATCTTCTTTCTC-3' | 23 (SEQ ID No.19) |
| F156Rev | 5'-TTCTTAGGATTTCCACTCTGACTATGG-3' | 27 (SEQ ID No.20) |
| L5-C17Rev | 5'-TCTTTGTAGG<u>G</u>ATCCAAG<u>GG</u>AGTTGTAGC-3' | 29 (SEQ ID No.21) |
| L106-L130Rev | 5'-CCCCTGGTG<u>G</u>AATCTTCTTTCTC<u>GGA</u>-3' | 26 (SEQ ID No.22) |

Fig. 4

SEQUENCE LISTING

<160> NUMBER OF SEQ ID NOS: 26

<210> SEQ ID NO 1
<211> LENGTH: 166
<212> TYPE: PRT
<213> ORGANISM: Homo sapiens

<400> SEQUENCE: 1

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95
```

```
His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = Leu, Ser, Tyr, or Thr
<220> FEATURE:
<221> NAME/KEY: MISC_FEATURE
<222> LOCATION: (8)..(8)
<223> OTHER INFORMATION: Xaa = Phe, Ser, Tyr, or Thr
<220> FEATURE:
<221> NAME/KEY: MISC_FEATURE
<222> LOCATION: (15)..(15)
<223> OTHER INFORMATION: Xaa = Phe, Ser, Tyr, or Thr
<220> FEATURE:
<221> NAME/KEY: MISC_FEATURE
<222> LOCATION: (47)..(47)
<223> OTHER INFORMATION: Xaa = Leu, Ser, Tyr, or Thr
<220> FEATURE:
<221> NAME/KEY: MISC_FEATURE
<222> LOCATION: (50)..(50)
<223> OTHER INFORMATION: Xaa = Phe, Ser, Tyr, or Thr
<220> FEATURE:
<221> NAME/KEY: MISC_FEATURE
<222> LOCATION: (106)..(106)
<223> OTHER INFORMATION: Xaa = Leu, Ser, Tyr, or Thr
<220> FEATURE:
<221> NAME/KEY: MISC_FEATURE
<222> LOCATION: (111)..(111)
<223> OTHER INFORMATION: Xaa = Phe, Ser, Tyr, or Thr
<220> FEATURE:
<221> NAME/KEY: MISC_FEATURE
<222> LOCATION: (116)..(116)
<223> OTHER INFORMATION: Xaa = Leu, Ser, Tyr, or Thr
<220> FEATURE:
<221> NAME/KEY: MISC_FEATURE
<222> LOCATION: (120)..(120)
<223> OTHER INFORMATION: Xaa = Leu, Ser, Tyr, or Thr
<220> FEATURE:
<221> NAME/KEY: MISC_FEATURE
<222> LOCATION: (151)..(151)
<223> OTHER INFORMATION: Xaa = Leu, Ser, Tyr, or Thr

<400> SEQUENCE: 2

Met Ser Tyr Asn Xaa Leu Gly Xaa Leu Gln Arg Ser Ser Asn Xaa Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Xaa Gln
        35                  40                  45

Gln Xaa Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
```

-continued 85 90 95

His Leu Lys Thr Val Leu Glu Glu Lys Xaa Glu Lys Glu Asp Xaa Thr
100 105 110

Arg Gly Lys Xaa Met Ser Ser Xaa His Leu Lys Arg Tyr Tyr Gly Arg
115 120 125

Ile Leu His Tyr Leu Lys Ala Lys Glu Tyr Ser His Cys Ala Trp Thr
130 135 140

Ile Val Arg Val Glu Ile Xaa Arg Asn Phe Tyr Phe Ile Asn Arg Leu
145 150 155 160

Thr Gly Tyr Leu Arg Asn
165

<210> SEQ ID NO 3
<211> LENGTH: 166
<212> TYPE: PRT
<213> ORGANISM: Homo sapiens

<400> SEQUENCE: 3

Met Ser Tyr Asn Ser Leu Gly Ser Leu Gln Arg Ser Ser Asn Ser Gln
1 5 10 15

Cys Gln Lys Leu Leu Trp Gln Leu Asn Gly Arg Leu Glu Tyr Cys Leu
20 25 30

Lys Asp Arg Met Asn Phe Asp Ile Pro Glu Glu Ile Lys Gln Ser Gln
35 40 45

Gln Ser Gln Lys Glu Asp Ala Ala Leu Thr Ile Tyr Glu Met Leu Gln
50 55 60

Asn Ile Phe Ala Ile Phe Arg Gln Asp Ser Ser Ser Thr Gly Trp Asn
65 70 75 80

Glu Thr Ile Val Glu Asn Leu Leu Ala Asn Val Tyr His Gln Ile Asn
85 90 95

His Leu Lys Thr Val Leu Glu Glu Lys Ser Glu Lys Glu Asp Ser Thr
100 105 110

Arg Gly Lys Ser Met Ser Ser Ser His Leu Lys Arg Tyr Tyr Gly Arg
115 120 125

Ile Leu His Tyr Leu Lys Ala Lys Glu Tyr Ser His Cys Ala Trp Thr
130 135 140

Ile Val Arg Val Glu Ile Leu Arg Asn Phe Tyr Ser Ile Asn Arg Leu
145 150 155 160

Thr Gly Tyr Leu Arg Asn
165

<210> SEQ ID NO 4
<211> LENGTH: 25
<212> TYPE: DNA
<213> ORGANISM: Artificial sequence
<220> FEATURE:
<223> OTHER INFORMATION: Description of Artificial Sequence: Primer for Homo sapiens beta -interferon, wherein nucleotides are altered to substitute a serine for another amino acid
<220> FEATURE:
<221> NAME/KEY: mutation
<222> LOCATION: (3)..(4)
<223> OTHER INFORMATION: Leu to Ser mutation

<400> SEQUENCE: 4
ctcccttgga ttcctacaaa gaagc 25

<210> SEQ ID NO 5
<211> LENGTH: 25

```
<212> TYPE: DNA
<213> ORGANISM: artificial sequence
<220> FEATURE:
<223> OTHER INFORMATION: Description of Artificial Sequence: Primer for
      Homo sapiens beta -interferon, wherein nucleotides are altered to
      substitute a serine for another amino acid
<220> FEATURE:
<221> NAME/KEY: mutation
<222> LOCATION: (12)..(12)
<223> OTHER INFORMATION: Phe to Ser mutation

<400> SEQUENCE: 5
cttgcttgga tccctacaaa gaagc                                         25

<210> SEQ ID NO 6
<211> LENGTH: 28
<212> TYPE: DNA
<213> ORGANISM: artificial sequence
<220> FEATURE:
<223> OTHER INFORMATION: Description of Artificial Sequence: Primer for
      Homo sapiens beta -interferon, wherein nucleotides are altered to
      substitute a serine for another amino acid
<220> FEATURE:
<221> NAME/KEY: mutation
<222> LOCATION: (11)..(11)
<223> OTHER INFORMATION: Phe to Ser mutation
<220> FEATURE:
<221> NAME/KEY: mutation
<222> LOCATION: (17)..(18)
<223> OTHER INFORMATION: Cys to Ser mutation

<400> SEQUENCE: 6
agcagcaatt ctcagtccca gaagctcc                                      28

<210> SEQ ID NO 7
<211> LENGTH: 28
<212> TYPE: DNA
<213> ORGANISM: Artificial sequence
<220> FEATURE:
<223> OTHER INFORMATION: Description of Artificial Sequence: Primer for
      Homo sapiens beta -interferon, wherein nucleotides are altered to
      substitute a serine for another amino acid
<220> FEATURE:
<221> NAME/KEY: mutation
<222> LOCATION: (17)..(18)
<223> OTHER INFORMATION: Cys to Ser mutation

<400> SEQUENCE: 7
agcagcaatt ttcagtccca gaagctcc                                      28

<210> SEQ ID NO 8
<211> LENGTH: 27
<212> TYPE: DNA
<213> ORGANISM: Artificial sequence
<220> FEATURE:
<223> OTHER INFORMATION: Description of Artificial Sequence: Primer for
      Homo sapiens beta-interferon, wherein nucleotides are altered to
      substitute a serine for another amino acid
<220> FEATURE:
<221> NAME/KEY: mutation
<222> LOCATION: (9)..(11)
<223> OTHER INFORMATION: Leu to Ser mutation

<400> SEQUENCE: 8
ttaagcagtc ccagcagttc cagaagg                                       27

<210> SEQ ID NO 9
<211> LENGTH: 27
<212> TYPE: DNA
<213> ORGANISM: Artificial sequence
<220> FEATURE:
```

```
<223> OTHER INFORMATION: Description of Artificial Sequence:  Primer for
      Homo sapiens beta -interferon, wherein nucleotides are altered to
      substitute a serine for another amino acid
<220> FEATURE:
<221> NAME/KEY: mutation
<222> LOCATION: (19)..(19)
<223> OTHER INFORMATION: Phe to Ser mutation

<400> SEQUENCE: 9
ttaagcagct gcagcagtcc cagaagg                                        27

<210> SEQ ID NO 10
<211> LENGTH: 30
<212> TYPE: DNA
<213> ORGANISM: Artificial sequence
<220> FEATURE:
<223> OTHER INFORMATION: Description of Artificial Sequence:  Primer for
      Homo sapiens beta -interferon, wherein nucleotides are altered to
      substitute a serine for another amino acid
<220> FEATURE:
<221> NAME/KEY: mutation
<222> LOCATION: (10)..(12)
<223> OTHER INFORMATION: Leu to Ser mutation

<400> SEQUENCE: 10
gaagaaaaat ccgagaaaga agatttcacc                                     30

<210> SEQ ID NO 11
<211> LENGTH: 30
<212> TYPE: DNA
<213> ORGANISM: Artificial sequence
<220> FEATURE:
<223> OTHER INFORMATION: Description of Artificial Sequence:  Primer for
      Homo sapiens beta -interferon, wherein nucleotides are altered to
      substitute a serine for another amino acid
<220> FEATURE:
<221> NAME/KEY: mutation
<222> LOCATION: (26)..(26)
<223> OTHER INFORMATION: Phe to Ser mutation

<400> SEQUENCE: 11
gaagaaaaac tggagaaaga agattccacc                                     30

<210> SEQ ID NO 12
<211> LENGTH: 25
<212> TYPE: DNA
<213> ORGANISM: Artificial sequence
<220> FEATURE:
<223> OTHER INFORMATION: Description of Artificial Sequence:  Primer for
      Homo sapiens beta -interferon, wherein nucleotides are altered to
      substitute a serine for another amino acid
<220> FEATURE:
<221> NAME/KEY: mutation
<222> LOCATION: (5)..(6)
<223> OTHER INFORMATION: Leu to Ser mutation

<400> SEQUENCE: 12
aaaatccatg agcagtctgc acctg                                          25

<210> SEQ ID NO 13
<211> LENGTH: 25
<212> TYPE: DNA
<213> ORGANISM: Artificial sequence
<220> FEATURE:
<223> OTHER INFORMATION: Description of Artificial Sequence:  Primer for
      Homo sapiens beta -interferon, wherein nucleotides are altered to
      substitute a serine for another amino acid
<220> FEATURE:
<221> NAME/KEY: mutation
<222> LOCATION: (17)..(19)
<223> OTHER INFORMATION: Leu to Ser mutation
```

<400> SEQUENCE: 13
aaaactcatg agcagttccc acctg                                   25

<210> SEQ ID NO 14
<211> LENGTH: 28
<212> TYPE: DNA
<213> ORGANISM: Artificial sequence
<220> FEATURE:
<223> OTHER INFORMATION: Description of Artificial Sequence: Primer for
      Homo sapiens beta -interferon, wherein nucleotides are altered to
      substitute a serine for another amino acid
<220> FEATURE:
<221> NAME/KEY: mutation
<222> LOCATION: (10)..(10)
<223> OTHER INFORMATION: Phe to Ser mutation

<400> SEQUENCE: 14
acttttactc cattaacaga cctacagg                                28

<210> SEQ ID NO 15
<211> LENGTH: 25
<212> TYPE: DNA
<213> ORGANISM: Artificial sequence
<220> FEATURE:
<223> OTHER INFORMATION: Description of Artificial Sequence: Reverse
      primer for Homo sapiens beta-interferon, wherein nucleotides in
      the forward primer are altered to substitute a serine for another
      amino acid

<400> SEQUENCE: 15
ttgtagctca tatgtaagta tttcc                                   25

<210> SEQ ID NO 16
<211> LENGTH: 29
<212> TYPE: DNA
<213> ORGANISM: Artificial sequence
<220> FEATURE:
<223> OTHER INFORMATION: Description of Artificial Sequence: Reverse
      primer for Homo sapiens beta-interferon, wherein nucleotides in
      the forward primer are altered to substitute a serine for another
      amino acid

<400> SEQUENCE: 16
tctttgtagg aatccaagca agttgtagc                               29

<210> SEQ ID NO 17
<211> LENGTH: 27
<212> TYPE: DNA
<213> ORGANISM: Artificial sequence
<220> FEATURE:
<223> OTHER INFORMATION: Description of Artificial Sequence: Reverse
      primer for Homo sapiens beta-interferon, wherein nucleotides in
      the forward primer are altered to substitute a serine for another
      amino acid

<400> SEQUENCE: 17
tctcctcagg gatgtcaaag ttcatcc                                 27

<210> SEQ ID NO 18
<211> LENGTH: 27
<212> TYPE: DNA
<213> ORGANISM: Artificial sequence
<220> FEATURE:
<223> OTHER INFORMATION: Description of Artificial Sequence: Reverse
      primer for Homo sapiens beta-interferon, wherein nucleotides in
      the forward primer are altered to substitute a serine for another
      amino acid

```
<400> SEQUENCE: 18
caggactgtc ttcagatggt ttatctg                                      27

<210> SEQ ID NO 19
<211> LENGTH: 23
<212> TYPE: DNA
<213> ORGANISM: Artificial sequence
<220> FEATURE:
<223> OTHER INFORMATION: Description of Artificial Sequence:  Reverse
      primer for Homo sapiens beta-interferon, wherein nucleotides in
      the forward primer are altered to substitute a serine for another
      amino acid

<400> SEQUENCE: 19
cccctggtga aatcttcttt ctc                                          23

<210> SEQ ID NO 20
<211> LENGTH: 27
<212> TYPE: DNA
<213> ORGANISM: Artificial sequence
<220> FEATURE:
<223> OTHER INFORMATION: Description of Artificial Sequence:  Reverse
      primer for Homo sapiens beta-interferon, wherein nucleotides in
      the forward primer are altered to substitute a serine for another
      amino acid

<400> SEQUENCE: 20
ttcttaggat ttccactctg actatgg                                      27

<210> SEQ ID NO 21
<211> LENGTH: 29
<212> TYPE: DNA
<213> ORGANISM: Artificial sequence
<220> FEATURE:
<223> OTHER INFORMATION: Description of Artificial Sequence:  Reverse
      primer for Homo sapiens beta-interferon, wherein nucleotides are
      altered to substitute a serine for another amino acid
<220> FEATURE:
<221> NAME/KEY: mutation
<222> LOCATION: (11)..(11)
<223> OTHER INFORMATION: Leu to Ser mutation
<220> FEATURE:
<221> NAME/KEY: mutation
<222> LOCATION: (19)..(20)
<223> OTHER INFORMATION: Cys to Ser mutation

<400> SEQUENCE: 21
tctttgtagg gatccaaggg agttgtagc                                    29

<210> SEQ ID NO 22
<211> LENGTH: 26
<212> TYPE: DNA
<213> ORGANISM: Artificial sequence
<220> FEATURE:
<223> OTHER INFORMATION: Description of Artificial Sequence:  Reverse
      primer for Homo sapiens beta-interferon, wherein nucleotides are
      altered to substitute a serine for another amino acid
<220> FEATURE:
<221> NAME/KEY: mutation
<222> LOCATION: (10)..(10)
<223> OTHER INFORMATION: Leu to Ser mutation
<220> FEATURE:
<221> NAME/KEY: mutation
<222> LOCATION: (24)..(26)
<223> OTHER INFORMATION: Leu to Ser mutation

<400> SEQUENCE: 22
cccctggtgg aatcttcttt ctcgga                                       26
```

```
<210> SEQ ID NO 23
<211> LENGTH: 166
<212> TYPE: PRT
<213> ORGANISM: Homo sapiens

<400> SEQUENCE: 23

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Ser Gln
        35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 24
<211> LENGTH: 166
<212> TYPE: PRT
<213> ORGANISM: Homo sapiens

<400> SEQUENCE: 24

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Ser Gln
        35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
```

-continued

```
                165

<210> SEQ ID NO 25
<211> LENGTH: 166
<212> TYPE: PRT
<213> ORGANISM: Homo sapiens

<400> SEQUENCE: 25

Met Ser Tyr Asn Ser Leu Gly Ser Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Ser Gln
        35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 26
<211> LENGTH: 166
<212> TYPE: PRT
<213> ORGANISM: Homo sapiens

<400> SEQUENCE: 26

Met Ser Tyr Asn Ser Leu Gly Ser Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Ser Gln
        35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
```

```
                                    -continued
145                 150              155              160
Thr Gly Tyr Leu Arg Asn
                165
```

RECOMBINANT HUMAN BETA INTERFERON WITH ENHANCED SOLUBILITY

CROSS-REFERENCES TO RELATED APPLICATIONS

This application is a U.S. national application of international application serial No. PCT/EP98/02238 filed Apr. 16, 1998, which claims priority to German serial No. 197 17 864.2 filed Apr. 23, 1997.

The invention pertains to variants of human recombinant beta-interferon with improved solubility.

Beta-interferon is a regulatory protein which leads to activation of genes by binding receptors. As a result, antiviral, antiproliferative and further biological activities are mediated in the cell.

The inteferons, as is also the case with the interleukins, belong to the class of cytokines and are subdivided into different classes:

Type I interferon (alpha, beta, omega, tau) and Type II (gamma)

Human beta-interferon is a protein with a molecular weight of 22 kDa and 166 amino acid residues. It is formed primarily in fibroblasts during attack by a virus and possesses antiviral, antiproliferative and further biological activities. The amino acid sequence of human beta-interferon was first published by Taniguchi et al. (1980), Gene Ed. 10, pages 11 through 15, and is illustrated in FIG. 1.

Beta-interferon, which is produced from bacterial cells or mammalian cells by genetic engineering, is being used successfully in the treatment of multiple sclerosis, a previously incurable disease in a large group of patients. However, the very high hydrophobicity of the protein, which causes very poor solubility of recombinant human beta-interferon, proves to be problematical for the production and processing of recombinant human beta-interferon.

The problem for the present invention is to make available variants of recombinant human beta-interferon whose solubility is improved in polar media, such as e.g. aqueous liquids. In addition an objective of this invention is to indicate processes for manufacturing and possibilities for using variants of recombinant human beta-interferon with higher solubility in polar media such as aqueous liquids.

This problem is solved by the recombinant human beta-interferon in accordance with claim 1, its use in accordance with claim 5 and its manufacture in accordance with claim 6 or 7.

In accordance with claim 1, at least one of the following ten hydrophobic amino acids in known human beta-interferon is exchanged for a hydrophilic amino acid: Leu 5, Phe 8, Phe 15, Leu 47, Phe 50, Leu 106, Phe 111, Leu 120 or Phe 156 (SED ID No.2). Thus the invention pertains to individual mutations as well as to all the possible combinations of these individual amino acid exchanges.

The designated amino acids are essentially located on the surface of human beta-interferon and they take up a relatively large proportion of the surface there. The exchange of these amino acids therefore leads to more than a proportionately large improvement in the hydrophilic character of the surface of recombinant human beta-interferon and it therefore increases the solubility of this protein in polar media, such as e.g. aqueous liquids. As a result of its increased hydrophilicity, the recombinant human beta-interferon in accordance with the invention is considerably simpler to handle in production as well as during its processing to give an active substance.

The production of the variants of recombinant human beta-interferon in accordance with the invention takes place in a generally known, conventional way with the help of microorganisms, e.g. in an *Escherichia coli* culture which has been provided with the gene for one of the proteins in accordance with the invention. The production of these microorganisms, which have been changed by means of genetic engineering, also takes place in a generally known way with the help of classical genetic engineering mutagenesis procedures for the exchange of the corresponding amino acids for hydrophilic amino acids and their synthesis will therefore be dispensed with at this juncture.

The proteins in accordance with the invention find use for the manufacture of medicinal drugs, e.g. for combatting multiple sclerosis, as well as fine chemicals for in vitro experiments or for measurements of interferon levels. The improved hydrophilicity of these proteins thereby simplifies their manufacture, transportation, storage and application in the form of a medicinal drug or fine chemical.

Advantageous further developments of the proteins in accordance with the invention are given in the dependent claims.

Exchange for the amino acids serine, tyrosine and threonine is especially advantageous and, with one hydroxy group each, these are especially hydrophilic.

As a result of its small size, serine is especially suitable for exchange since especially slight steric changes in the protein are associated with it.

The amino acid sequence of native recombinant human beta-interferon, in which the abovementioned ten amino acids are electively exchanged for serine, is illustrated in FIG. 2. These exchangeable amino acids are represented by Xaa. If these amino acids are exchanged, then the hydrophilicity of the surface of recombinant human beta-interferon is very much improved whereas only slight impairment arises in terms of the functionality and the efficacy of human recombinant beta-interferon.

An especially advantageous further development is illustrated in FIG. 3 in which all of the abovementioned ten amino acids have been exchanged here for serine so that an especially marked increase in the hydrophilicity of the surface of recombinant human beta-interferon results.

An example of a variant of human recombinant beta-interferon in accordance with the invention is given in the following sections:

FIG. 1 shows native human recombinant beta-interferon;

FIG. 2 shows the variants of recombinant human beta-interferon in accordance with the invention;

FIG. 3 shows a recombinant human beta-interferon [variant] in accordance with the invention; and FIG. 4 shows primers for the mutagenesis for the manufacture of beta-interferon in accordance with the invention.

As already described above, FIG. 1 describes native human recombinant beta-interferon in the form in which it can already be manufactured currently with the help of known molecular biological and bio-technical possibilities.

The sequence of native human recombinant beta-interferon is illustrated in FIG. 2 in which Xaa designates those amino acids which can be exchanged for an amino acid with at least one hydroxy group (advantageously serine, tyrosine and/or threonine) and hence result in a recombinant human beta-interferon [variant] in accordance with the invention which possesses increased surface hydrophilicity.

By way of example, all ten individual variants of beta-interferon have been manufactured in which Leu (5), Phe (8), Phe (15), Leu (47), Phe (50), Leu (106), Phe (111), Leu (116), Leu (120) or Phe (156) (SEQ ID No.2) were exchanged for serine, whereby, in particular, the variants with exchange of the amino acids Leu (5), Phe (8), Leu (47), Phe (50), Leu (106), Phe (111), Leu (116) and Leu (120) (SEQ ID No.26) relative to native beta-interferon, and also these variants of the Cys-17-Ser variant of human beta-interferon, excel by virtue of comparable biological activity.

FIG. 3 shows an example of a human recombinant beta-interferon [variant] in which the following amino acids have been exchanged for serine:

Leu (5), Phe (8), Phe (15), Leu (47), Phe (50), Leu (106), Phe (111), Leu (116), Leu (120) and Phe (156) (SEQ ID No.3). In the case of this variant of recombinant human beta-interferon, especially high hydrophilicity of the surface of the protein results and, hence, especially good solubility in aqueous solutions.

For example, the multiple variant with amino acid exchanges at positions 4, 50, 106, 111, 116 and 120 (SEQ ID No.23) also shows activity which corresponds to the beta-interferon starting protein, with a Cys17Ser exchange (SEQ ID No.24), which was used in this example.

The manufacture of organisms with a gene, which has been changed in accordance with the invention, for human recombinant beta-interferon takes place by means of classical mutagenesis procedures.

Mutagenesis takes place by means of a PCR (polymerase chain reaction). The mutations are introduced via synthetic oligonucleotides. Plasmid DNA with the beta-INF gene serves as the template. The entire plasmid was replicated with the PCR method which was used here. The selection of the PCR fragments takes place by means of restriction digestion of the entire PCR mixture with the enzyme DpnI. This enzyme recognizes only methylated interfaces. Since fragments, which are produced in vitro by means of PCR, are unmethylated, only the template DNA is degraded by DpnI. After DpnI digestion, in the event of success, a fragment with the length of the linearized template remains behind and this carries the mutations. The PCR fragments that are produced are cloned and sequenced.

| PCR mixture (100 µl): | template DNA | 10 µg |
| | primers | 100 pmol each |
| | nucleotide mix | 200 µM per dNTP |
| | MgSO$_4$ | 2–6 mM |
| | DNA polymerase | 2.5 units |

| PCR protocol | Duration | Temperature |
| --- | --- | --- |
| step 1. | 4 min | 95° C. |
| step 2. | + enzyme | |
| step 3. | 45 sec | 95° C. |
| step 4. | 1 min | 55° C. |
| step 5. | 10 min | 68° C. |
| | | go to 3.(11x) |
| step 6. | 10 min | 68° C. |
| step 7. | | 4° C. |

The PCR was carried out in a Thermocycler PTC-200 (MJ Research company).

Two primers are necessary for each PCR, namely a "forward" primer and a "reverse" primer. The two primers follow one another directly but, in each case, they bind to different strands with the opposite orientation.

FIG. 4 illustrates primers which were used for the mutagenesis in order that the amino acid(s), that are designated on the left, be exchanged for serine in the gene product, i.e. the beta-interferon in accordance with the invention.

The last two primers alone contain reverse primer mutations. A PCR with these primers additionally introduces mutations without the previously inserted mutations 5/8 or 106/111 being relinquished. If the wild type is taken as a template, then four mutations can be introduced at the same time via the reverse primers (5–17 or as the case may be, 106–120).

What is claimed is:

1. A human recombinant beta-interferon wherein the amino acids Leu (47), Phe (50), Leu (106), Phe (111), Leu (116), and Leu (120) have been exchanged for serine and comprises the sequence as set forth in (SEQ ID No.23).

2. A human recombinant beta-interferon wherein the amino acids Cys (17), Leu (47), Phe (50), Leu (106), Phe (111), Leu (116), and Leu (120) have been exchanged for serine and comprises the sequence as set forth in (SEQ ID No.24).

3. A human recombinant beta-interferon wherein the amino acids Leu (5), Phe, (8) Cys (17), Leu (47), Phe (50), Leu (106), Phe (111), Leu (116), and Leu (120) have been exchanged for serine and comprises the sequence as set forth in (SEQ ID No.25).

4. A method of manufacturing a medicinal drug comprising the steps of:

obtaining a quantity of the beta-interferon according to claim 1, and dissolving the beta-interferon in an aqueous liquid.

5. A method of manufacturing a medicinal drug comprising the steps of:

obtaining a quantity of the beta-interferon according to claim 2, and dissolving the beta-interferon in an aqueous liquid.

6. A method of manufacturing a medicinal drug comprising the steps of:

obtaining a quantity of the beta-interferon according to claim 3, and dissolving the beta-interferon in an aqueous liquid.

7. A microorganism having a gene coding for the recombinant human beta-interferon of claim 1.

8. A microorganism having a gene coding for the recombinant human beta-interferon of claim 2.

9. A microorganism having a gene coding for the recombinant human beta-interferon of claim 3.

* * * * *